(12) United States Patent
Quine et al.

(10) Patent No.: US 7,972,869 B2
(45) Date of Patent: Jul. 5, 2011

(54) METHOD AND DEVICE FOR COLLECTING AND TRANSFERRING BIOHAZARD SAMPLES

(75) Inventors: Douglas B. Quine, Bethel, CT (US); Ashwani Sharma, Lincoln, ME (US); John E. Massucci, Eastchester, NY (US); Candace Lee Summers, Front Royal, VA (US)

(73) Assignee: Pitney Bowes Inc., Stamford, CT (US)

( * ) Notice: Subject to any disclaimer, the term of this patent is extended or adjusted under 35 U.S.C. 154(b) by 0 days.

(21) Appl. No.: 12/371,905

(22) Filed: Feb. 16, 2009

(65) Prior Publication Data

US 2009/0229384 A1    Sep. 17, 2009

Related U.S. Application Data

(63) Continuation-in-part of application No. 10/741,264, filed on Dec. 19, 2003, now Pat. No. 7,491,548.

(51) Int. Cl.
*G01N 33/00* (2006.01)

(52) U.S. Cl. .......................................... 436/177; 422/83

(58) Field of Classification Search .................... 422/50, 422/58, 68.1, 99, 100, 83, 88; 436/177
See application file for complete search history.

(56) References Cited

U.S. PATENT DOCUMENTS

| 6,463,815 B1 * | 10/2002 | Tallentire et al. | 73/863.23 |
| 2004/0045342 A1 * | 3/2004 | Jones et al. | 73/37 |

* cited by examiner

*Primary Examiner* — Sam P Siefke
(74) *Attorney, Agent, or Firm* — George M. Macdonald; Charles R. Malandra, Jr.

(57) ABSTRACT

A method and system for collecting airborne particles and hydrating the collected particles for analysis. The airborne particles, which may be biological contaminants, are collected from a container containing one or more mailpieces. In the collection stage, a dry filter collection assembly is connected to the container and air is drawn out of the container through a dry filter. A hydration solution is then injected into the collection assembly to hydrate the collected particles. Part of the hydration solution containing the collected particles is caused to move out of the collection assembly to a test cartridge for further testing.

20 Claims, 11 Drawing Sheets

METHOD AND DEVICE FOR COLLECTING AND TRANSFERRING BIOHAZARD SAMPLES

RELATED APPLICATIONS

The present application is a continuation-in-part of commonly owned U.S. patent application Ser. No. 10/741,264, filed Dec. 19, 2003, entitled "Method And Device For Collecting And Transferring Biohazard Samples" in the names of Douglas B. Quine, Ashwani Sharma, and John E. Massucci that is hereby incorporated by reference in its entirety. The present application is related to commonly owned, U.S. Pat. No. 7,060,927 B1, issued Jun. 13, 2006, entitled Method and System For Isolating And Testing Biological Contaminants In Mail Packages and commonly owned, U.S. Pat. No. 7,340,970 B2, issued Mar. 11, 2008, entitled Method And Device For Isolating, Collecting And Transferring Hazardous Samples both of which are hereby incorporated by reference in their entirety.

FIELD OF THE INVENTION

The present invention relates generally to biohazard detection and, more particularly, to the transferring of a biohazard sample trapped in a filter to a detection system.

BACKGROUND OF THE INVENTION

In late 2001, several United States postal offices and other buildings were contaminated with *Bacillus anthracis* spores (anthrax) along the eastern United States, resulting in anthrax infection and death among several individuals. This incident was quite costly, not only in terms of the health-related impact, but also in the required decontamination efforts. Cleanup following the anthrax contamination proved to be difficult, labor intensive, and expensive. As this threat still exists, there exists a need to detect biological contaminants within the postal packages or other containers.

Detection of biohazards in the mail for culture or polymerase chain reaction (PCR) analysis requires collection of a sample. Because biological contaminants such as anthrax can be easily carried in the air, aerosolization is an effective way to stir up a sample for collection using a dry filter. Ultimately, however, current biological test systems, such as the PCR test unit made by Cepheid (Sunnyvale, Calif.), require wet samples to detect the existence of certain biological contaminants including anthrax. For analysis, it is therefore necessary to hydrate the dry filter sample and transfer it to the analysis system. However, existing wet sample collectors are expensive and the collection efficiency is low.

Thus, it is advantageous and desirable to provide a method and device for collecting dry biological contaminants and hydrating the collected samples for transfer.

SUMMARY OF THE INVENTION

The present invention provides a method and system for collecting particles that may be biological contaminants from the air in a mail container or the like. In the collection step, a dry filter collection assembly is connected to the mail container so as to allow air in the mail container to be drawn through a dry filter in the collection assembly. After this collection step, the filter collection assembly is disconnected from the mail container. A self-seal coupler, securely affixed to the collection assembly, is used to provide the connection between the collection assembly and the container, such that when the collection assembly is connected to the container, the coupler is opened to allow air to pass through. But when the collection assembly is disconnected from the container. The coupler becomes self-sealed, thereby preventing the collected particles in the collection assembly from leaking out.

After the filter collection assembly is disconnected from the mail container, a syringe or the like is used to inject a certain amount of hydration solution into the collection assembly to hydrate the collected particles. An agitation process is used to suspend at least part of the collected particles in the hydration solution. The filter collection assembly is connected to a test cartridge and part of the hydration solution containing the collected particles is caused to move out of the collection assembly to the test cartridge.

The present invention will become apparent upon reading the description taken in conjunction with FIGS. 1 to 7.

DETAILED DESCRIPTION OF THE INVENTION

Figure 1:
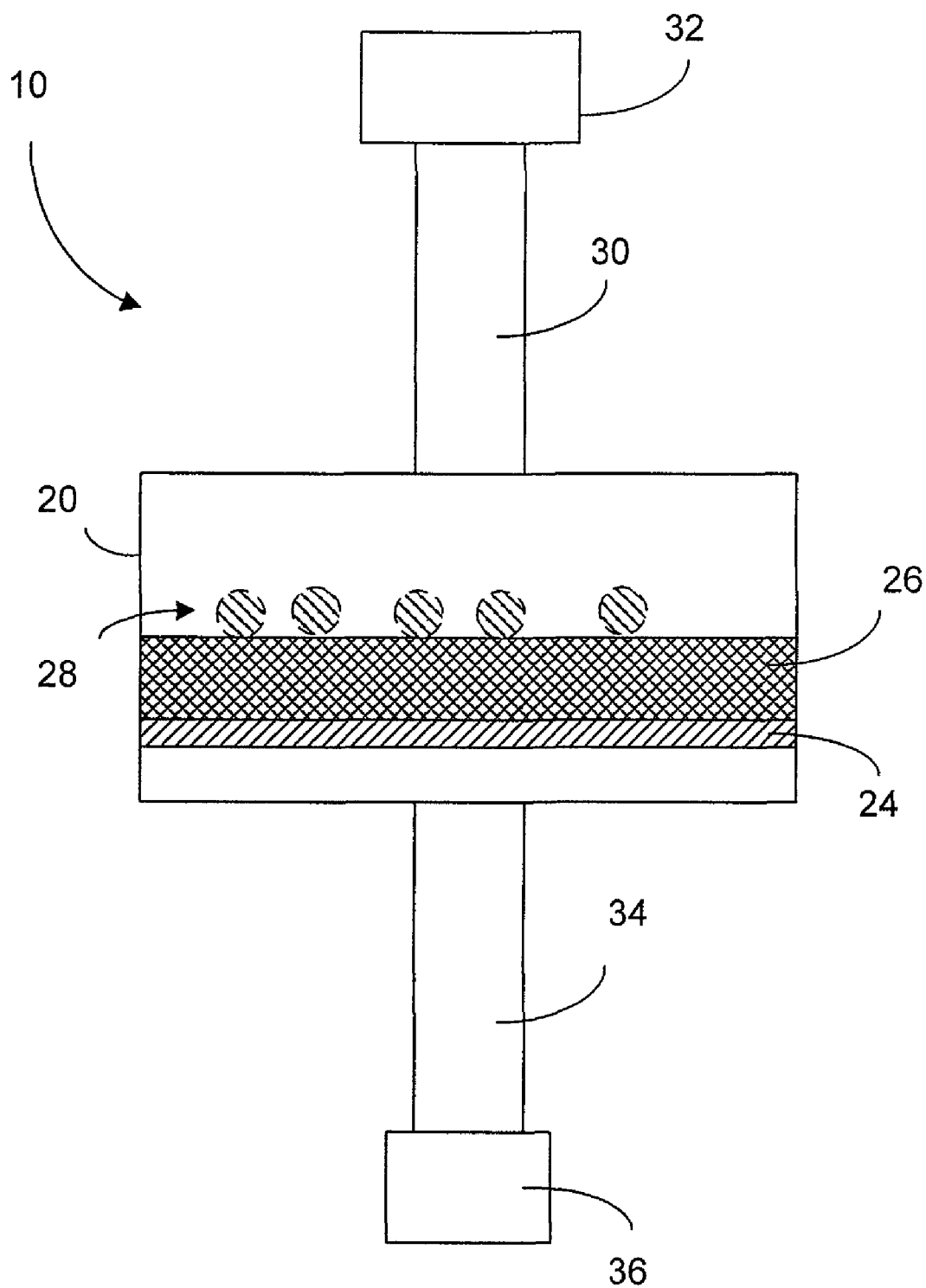
FIG. 1 is a schematic representation illustrating a filter collection assembly having a filter for collecting small airborne particles.
Figure 2:
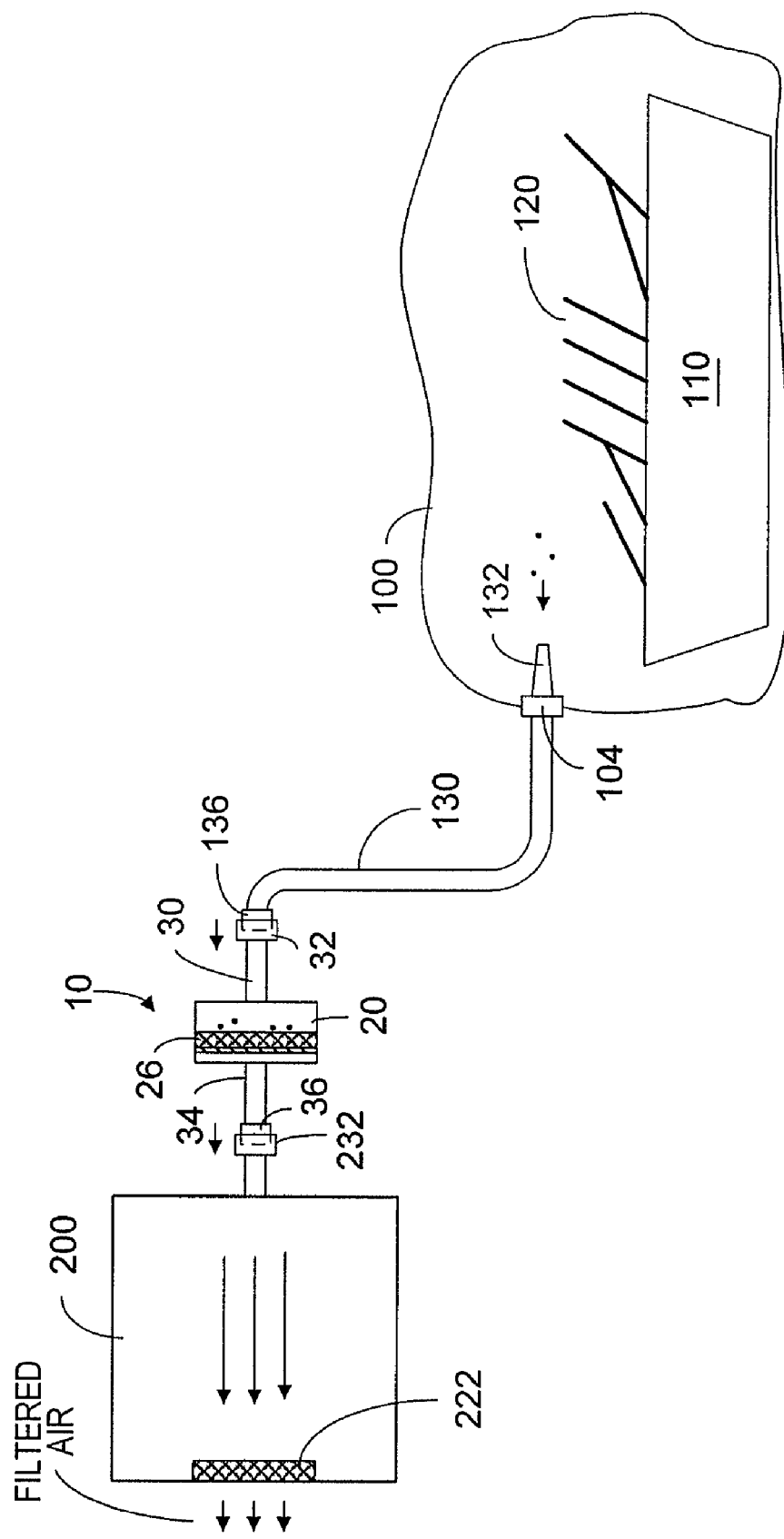
FIG. 2 is a schematic representation illustrating the filter collection assembly being connected to a mail container for collecting airborne particles in the mail container.

The present invention uses a dry filter collection assembly to collect the biological contaminants from a sealed mailbag or container containing one or more mailpieces. The collected samples in the assembly are hydrated and then transferred to a test cartridge for testing. According to the preferred embodiment of the present invention, the collection assembly has two passageways to allow air or liquid to pass through. As shown in FIG. 1, the collection assembly 10 has a filter chamber 20 operatively connected to a first passageway 30 and a second passageway 34. The filter chamber 20 comprises a filter holder 24 to support an air filter 26. The pores on the filter 26 are about 0.8 microns in diameter. The first passageway 30 is securely affixed to a first coupler 32, which is self-sealed. This means that the passageway is substantially airtight when the first coupler 32 is not engaged with a matching coupler. The second passageway 34 is securely affixed to a second coupler 36, which is also self-sealed. It is advantageous that the coupler 32 and the coupler 36 are different such that the collection assembly can only be connected to a certain device in a certain way. For example, one of the couplers 32, 34 is a "male" connector while the other is a "female" connector. Alternatively, they are of different shapes or sizes. The filter chamber may optionally contain a plurality of beads 28, as described later in conjunction with the agitation process. In the contaminant collection process, the first passageway 30 of the collection assembly 10 is operatively connected to a mailbag 100, which contains a mail tray 110 having one or more mailpieces 120. As shown in FIG. 2, the mailbag 100 has a tubing 130. One end of the tubing 130 is securely affixed to a self-sealed coupler 136. The other end of the tubing has an open inlet 132 to allow air to be drawn out from the mailbag 100 through the filter chamber 20 of the collection assembly 10, when the coupler 136 is engaged with the coupler 32. The open inlet 132 may be shaped like a "T" or have a number of orifices so that there are multiple sub-inlets to prevent blockage of air flow in the event that the end of the inlet touches the inner walls of the mailbag 100. The second passageway 34 of the collection assembly 10 is operatively connected to an air pump system 200 so as to allow air to be drawn out from the filter chamber 20 through an air filter 222, when the coupler 36 is engaged with a coupler 232 on the air pump system 200. It should be noted that the pores on the filter 222 should be small enough to prevent biological contaminants from passing through. For example, the filter 222 is a HEPA filter. Prior to or during the collection process, it would be advantageous to disturb the mailpieces 120 so as to cause the contaminants contained within the mailpieces to be released outside, or to cause the contaminants attached on the mailpieces to be dislodged and aerosolized. For example, the mailpieces can be disturbed by shaking the tray or by dropping the tray from a height of one foot. Preferably, the mailbag 100 is made of an anti-static material so that the released or dislodged contaminants do not become attached to the interior of the mailbag 100. When the coupler 136 and the coupler 32 are disconnected from each other, each of the couplers 136, 32 becomes self sealed. Likewise, when the coupler 36 and the coupler 232 are disconnected from each other, each of the couplers 36 and 232 becomes self-sealed. Thus, when the collection assembly 10 is disconnected from the mailbag 100 and the air pump system 200, the collection assembly 10 is sealed at both first and second passageways 30, 34. Thus, the collected contaminants in the filter chamber 20 are prevented from being released to the surroundings. Likewise, the coupler 136 is sealed, preventing the contaminants in the mailbag 100 from being released into the air. As for the air pump system 200, only the coupler 232 becomes self-sealed. Air can still pass through the filter 222. However, any unexpected contaminants collected inside the air pump system 200 are prevented from passing through the filter 222.

Figure 3A:
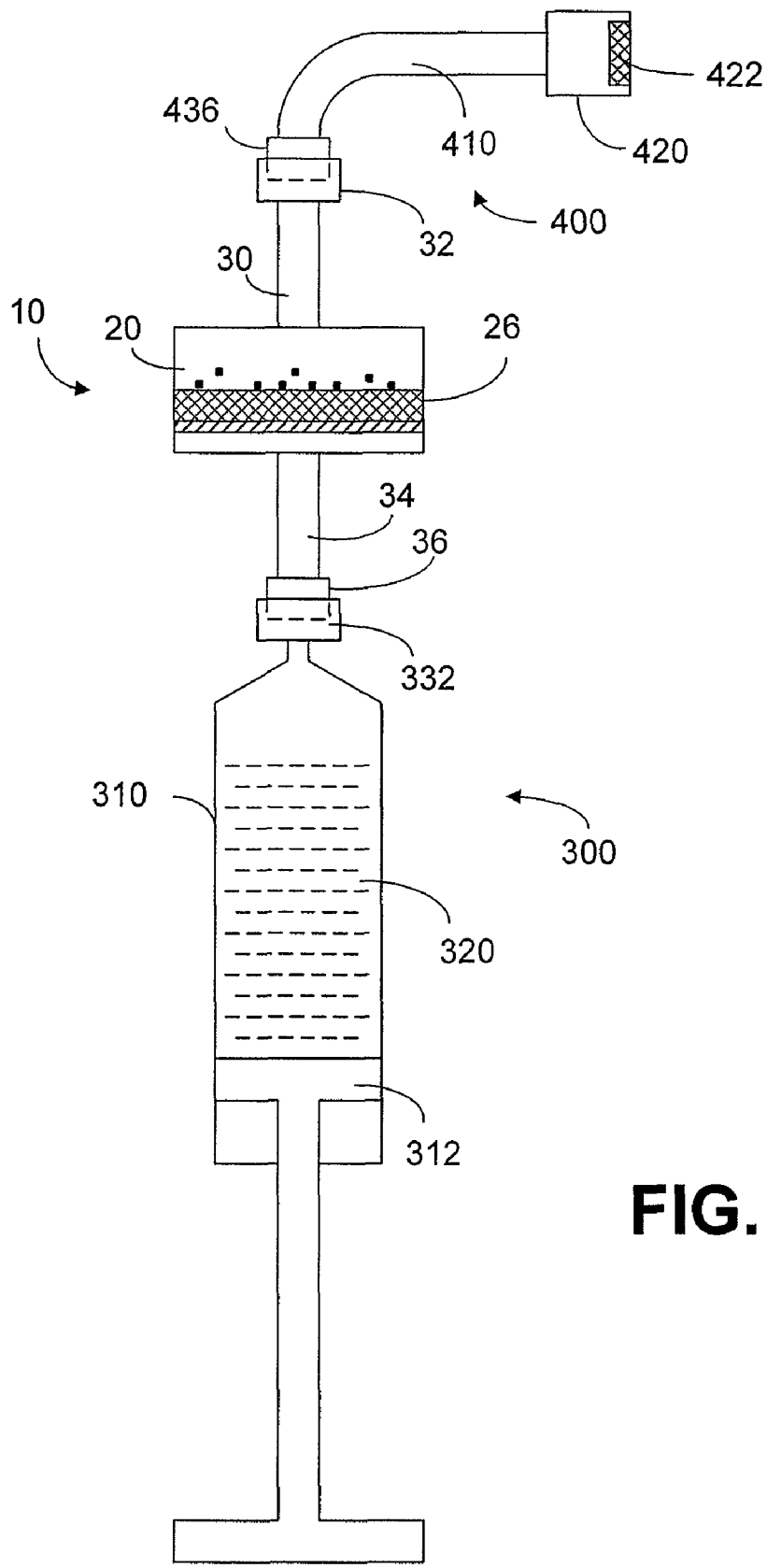
FIG. 3*a* is a schematic representation illustrating the filter collection assembly being connected to a liquid providing device containing a hydration solution.
Figure 3B:
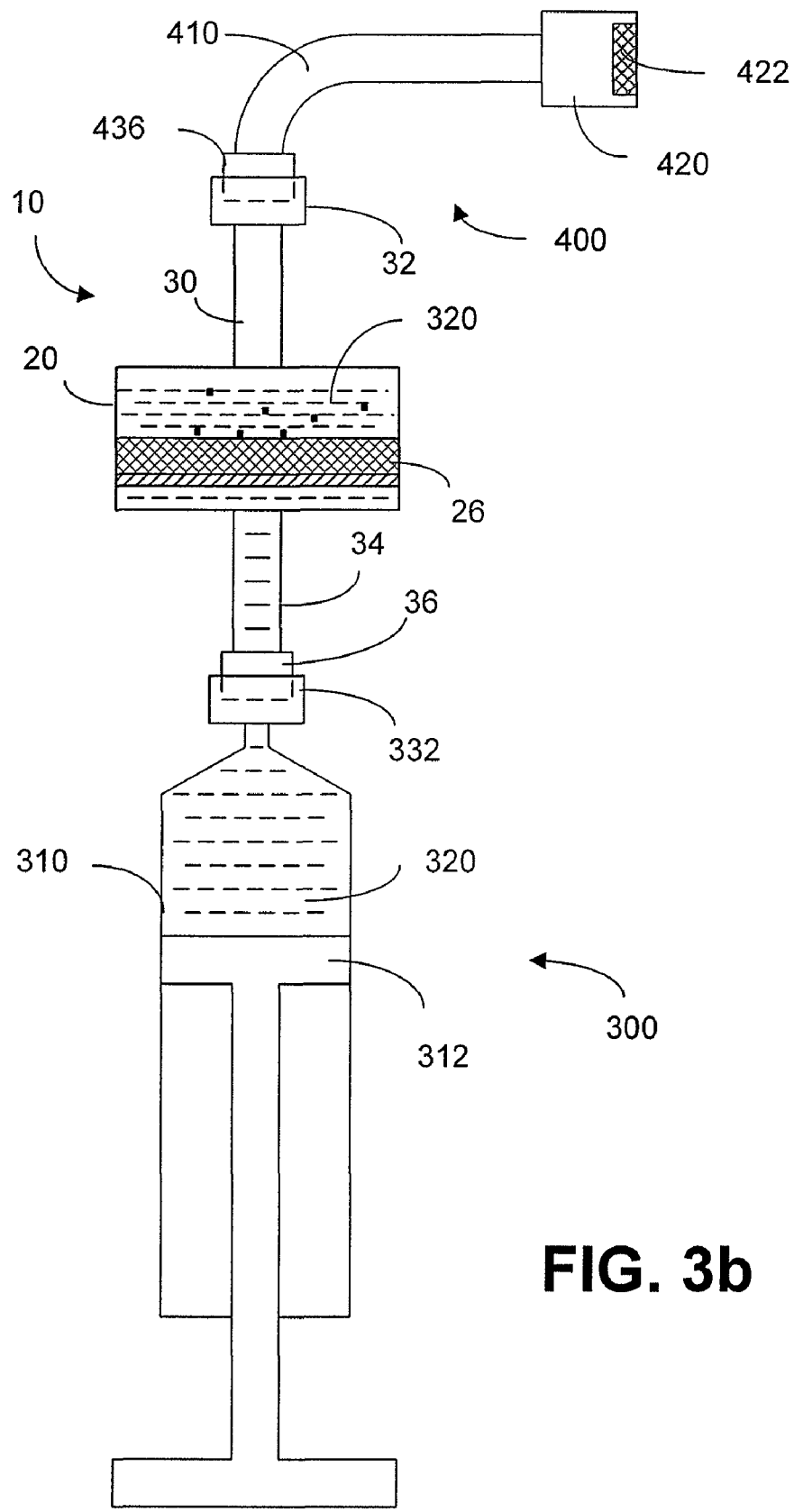
FIG. 3*b* is a schematic representation illustrating part of the hydration solution is injected into the filter collection assembly for hydrating the collected particles.

In the hydration process, the collection assembly 10 that has been disconnected from the mailbag 100 and the air pump system 200 is connected to a liquid injection system 300, as shown in FIG. 3a. The liquid injection system 300 has a liquid containing body 310 securely connected to a coupler 332, which can be engaged with the second coupler 36 of the collection assembly 10. For example, the liquid containing body 310 can be a syringe for injecting a desirable amount of hydration solution 320 backward into the filter chamber 20 through the second passageway 34 in order to flush the collected particles out of the filter 26 and into fluid suspension. On the other end of the collection assembly 10, the first passageway 30 is securely connected to a filter system 400 so as to allow the air inside the filter chamber 20 to be released when the hydration solution 320 is injected into the filter chamber 20. The filter assembly 400 is made of a tubing 410 having a coupler 436 on one end and a filter holder 420 on the other end. The filter holder 420 is used to support a HEPA filter 422 or the like. The coupler 436 is also self-sealed, but it can be engaged with the first coupler 32 so as to allow the air in the collection assembly 10 to exit through the tubing 410 and then the filter 422. Preferably, in the hydration process, the collection assembly 10 is only partially filled with the hydration solution 320 from the liquid containing body 310, as shown in FIG. 3b. For example, while the syringe is filled with a hydration solution, the plunger 312 is only partially depressed. As such, the remaining hydration solution can be used later in the transfer stage. At this stage, it is desirable to agitate the collection system 10 to cause the contaminants retained by the filter 26 to mix with the hydration solution in the filter chamber 20. Agitation can be carried out in many ways. For example, it is possible to place the edge of a vortex head in a vortex device in contact with the collection system 10 so as to allow the vortex head to shake the collection system 10 for 10 seconds, for example. Further, it may be desirable to preload or introduce a plurality of glass or plastic beads 28 into the filter chamber 20, as shown in FIG. 1, so that these beads can help dislodge the contaminants from the filter 26 during agitation.

Figure 4:
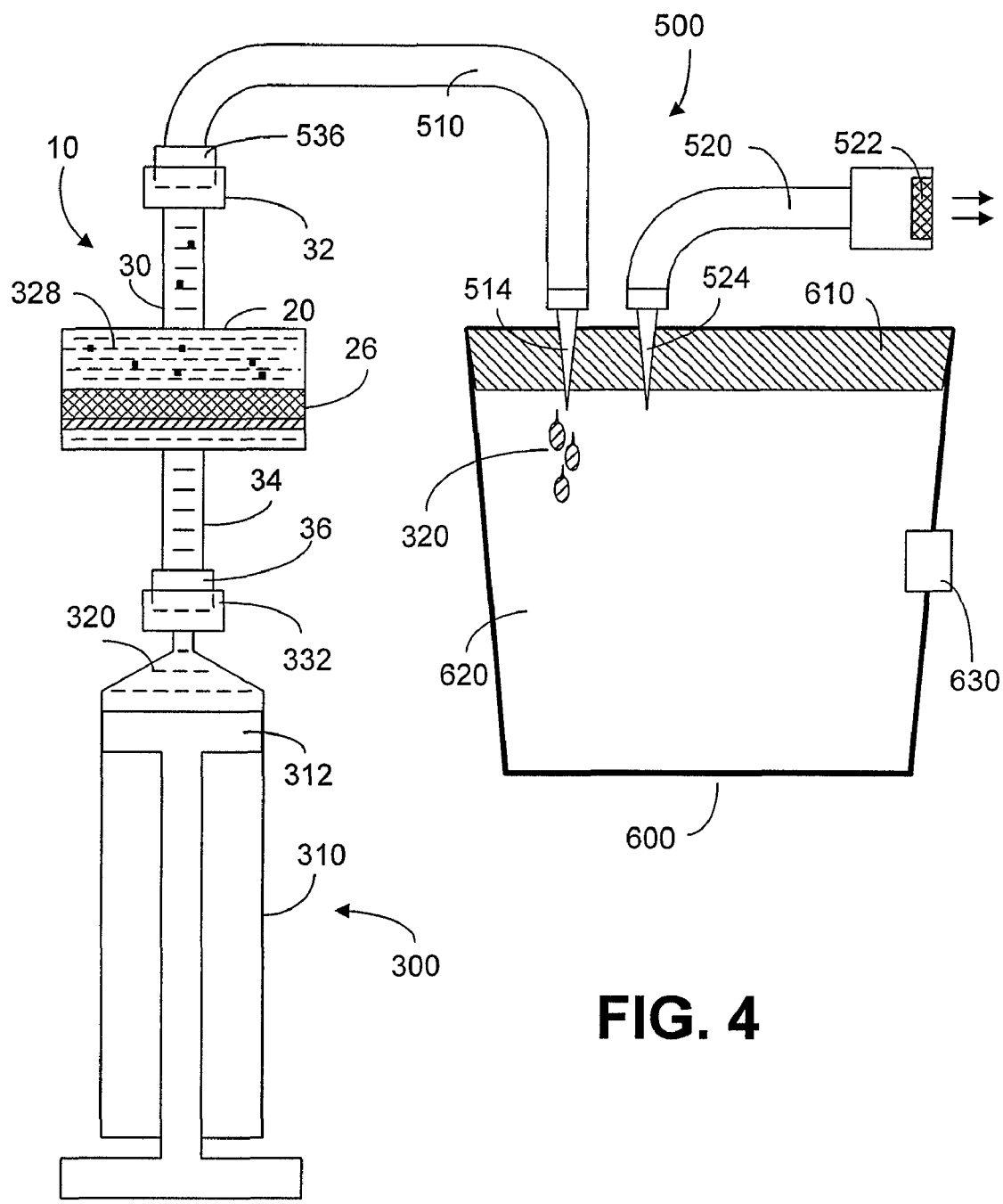
FIG. 4 is a schematic representation illustrating the liquid providing device is used to inject additional amount of hydration solution in order to move part of the hydration solution containing the collected particles into a test cartridge.

After agitation, the filter assembly 400 is removed from the collection assembly 10. A transfer system 500 is used to transfer part of the hydration solution 320 in the filter chamber 20 to a test cartridge 600 and a protruding test chamber 630 for data capture, which contains the chemistry 620 for PCR analysis. Preferably, the test cartridge 600 comprises a septum cover 610 for sealing the cartridge. The septum 610 allows an injection needle to puncture through. But when the needle is pulled off the septum, the septum becomes self-sealed. It should be noted that, in this transfer stage, the contaminants within the collection assembly 10 are in contact with a liquid. Thus, aerosolization of the biological contaminants is substantially avoided. As shown in FIG. 4, the transfer system 500 comprises an injection needle 514 connected to one end of a tubing 510, and a coupler 536 is connected to the other end. The transfer system 500 also comprises an air-venting needle 524 connected to one end of another tubing 520, and an air filter 522 connected to the other end. After the injection needle 514 and the air-venting needle 524 are adequately inserted into the test cartridge 600 through the septum cover 610, more hydration solution is injected into the collecting assembly 10 in order to push part of the hydration solution 320 inside the filter chamber 20 into the test cartridge 600. The displaced air is filtered by filter 522 to prevent release of any contaminants into the room. Before removing the test cartridge 600 from the transfer 500 so that the test cartridge can be placed in a test device for contaminant detection, it is preferable to withdraw the remaining liquid in the needle 514, the tubing 510 and the coupler 536 by backing off the syringe 300.

It should be noted that the test cartridge 600 for PCR analysis contains a plurality of separate chemical chambers for carrying out PCR processes. Thus, the injection needle 514 must be inserted through the septum cover 610 in the correct position so that the hydration solution is injected into the correct chamber. It is possible that the transfer system 500 has a keyed shape that fits the test cartridge only in a certain way so as to ensure the needle 514 punctures the septum in the correction position. Moreover, if the amount of hydration solution injected into the cartridge 600 is small, it may not be necessary to provide the air-venting needle 524 for air venting as long as the injection does not result in pressurizing the system. In an alternative embodiment, the transfer system 500 is also to preload the necessary chemical solutions into the test cartridge 600. One or more additional needles may be positioned on the transfer system 500 to introduce the chemical solutions into the chemical reaction chambers or to puncture the sealed bladders within these chemical reaction chambers for releasing the chemical solutions preloaded in the bladders.

Figure 5:
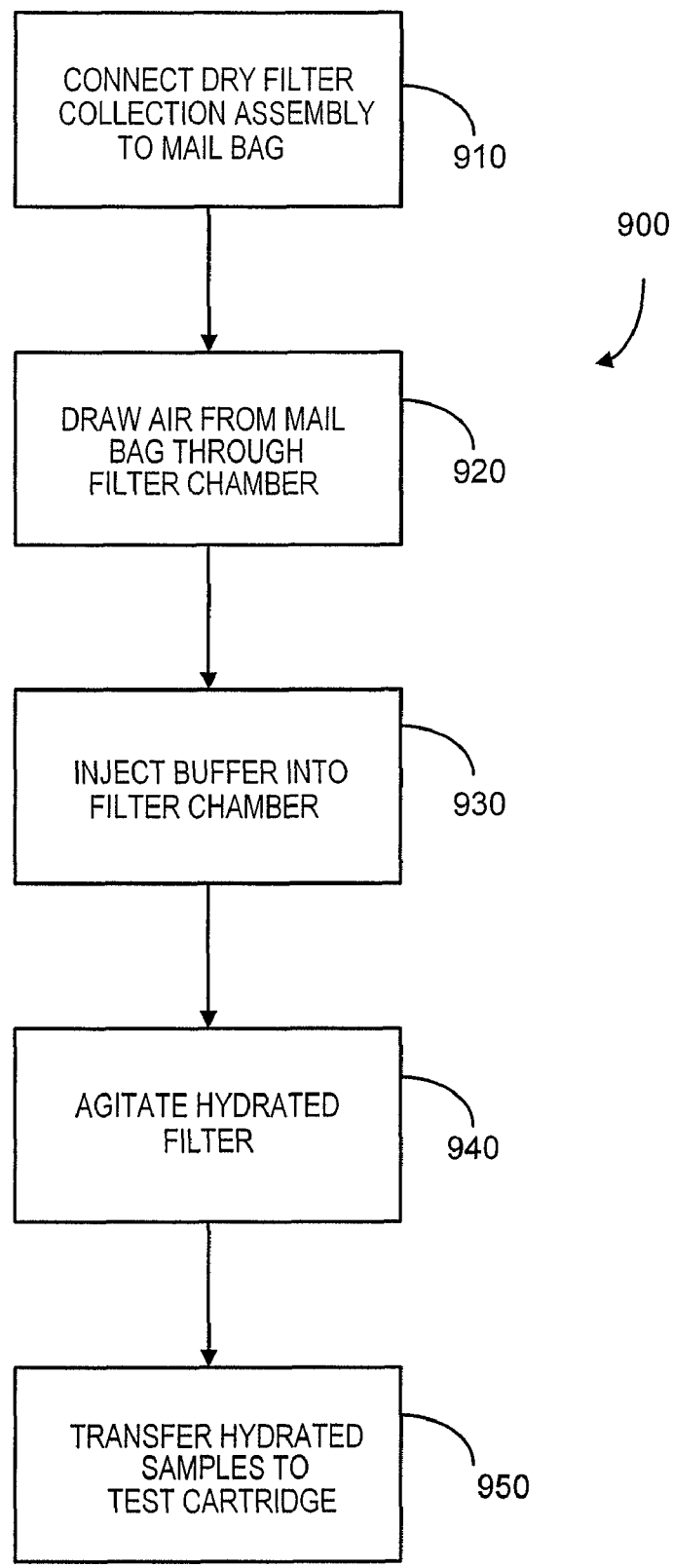
FIG. 5 is a flowchart illustrating the method of collecting particles and transferring the hydrated particles for testing, according to the present invention.

In sum, the method of collecting contaminants from a container such as mailbag and transferring the collected contaminants to a test cartridge, according to the present invention, is illustrated in the flowchart 900 in FIG. 5. As shown, a dry filter collection assembly 10 is connected to a mailbag 100 at step 910. The dry filter collection assembly 10 is also connected to an air pump system 200 so as to allow air in the mailbag to be drawn through the filter collection assembly 10 at step 920. After the filter collection assembly 10 is disconnected from the mailbag, a hydration solution is injected into the filter collection assembly at step 930. The filter collection assembly 10 is agitated, at step 940, in order to suspend at least part of the collected contaminants in the hydration solution. Finally, more liquid is injected into the filter collection assembly, at step 950, in order to push some of the hydration solution containing the contaminants into the test cartridge.

It should be noted that many components in the collection/transferring device, according to the present invention, are available as off-the-shelf products. For example, the dry filter collection assembly 10 can be modified from a filter cassette (Omega A0037503) supplied by BGI (Waltham, Mass.). The filter 26 is an Omega M083700P filter supplied by BGI. The filter is 37 mm MCE (mixed cellulose ester) 0.8 micron filter with a backing pad. This filter has been shown to capture substantially all anthrax spores. The coupler 32 is a self-seal male connector and the coupler 36 is a self seal female connector (62860-288 connector pair) made by VWR International (West Chester, Pa.) or PLCD170412 and mate made by Colder Products Corp (St. Paul, Minn.). The mailbag 100 is an aegis pink 36"×42"×0.004 anti-static poly bag with amines, Part No. 3508 supplied by Marathon Plastics, Inc. (Shelton, Conn.). The filter 222 is HEPA filter made by Whatman, Inc. (Clifton, N.J.). The test cartridge 600 is a 4 plex anthrax test cartridge made by Cepheid (Sunnyvale, Calif.) for use in a GeneXpert PCR 4-channel test system made by Cepheid. However, these products can be substituted by equivalents.

It should be noted that when the hydration solution is injected into the filter collection assembly at step 930, it is desirable that the amount of injected hydration solution is predetermined such that the filter chamber 20 is only partially filled. As such, the hydration solution in the filter chamber 20 can be easily agitated with a vortex device or the like. Accordingly, it is desirable to have a marking, indicative of the predetermined amount, provided on the syringe so that the person who depresses the plunger knows when to stop depressing the plunger. It is possible that a stopping device is used to limit the depressing of the plunger when needed. It is also possible to use two different syringes to provide a liquid to the filter chamber: one in the hydrating step and the other in the transferring step. It is also possible to move part of the hydration solution containing the particles out of the filter chamber to the test cartridge by injecting air into the filter chamber through the second passageway 34.

Figure 6A:
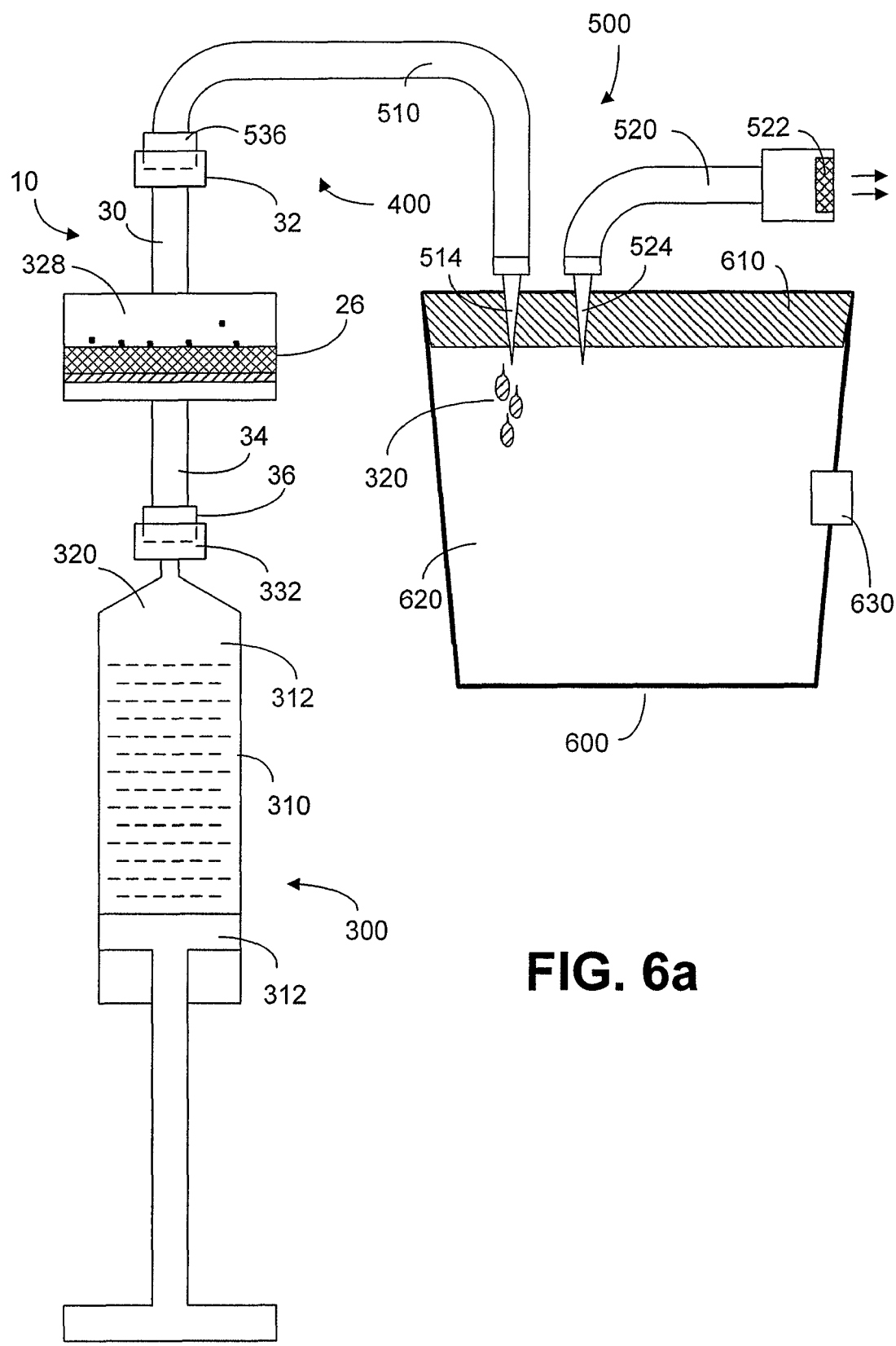
FIG. 6*a* is a schematic representation illustrating the liquid filter collection assembly being directly providing on a test cartridge.
Figure 6B:
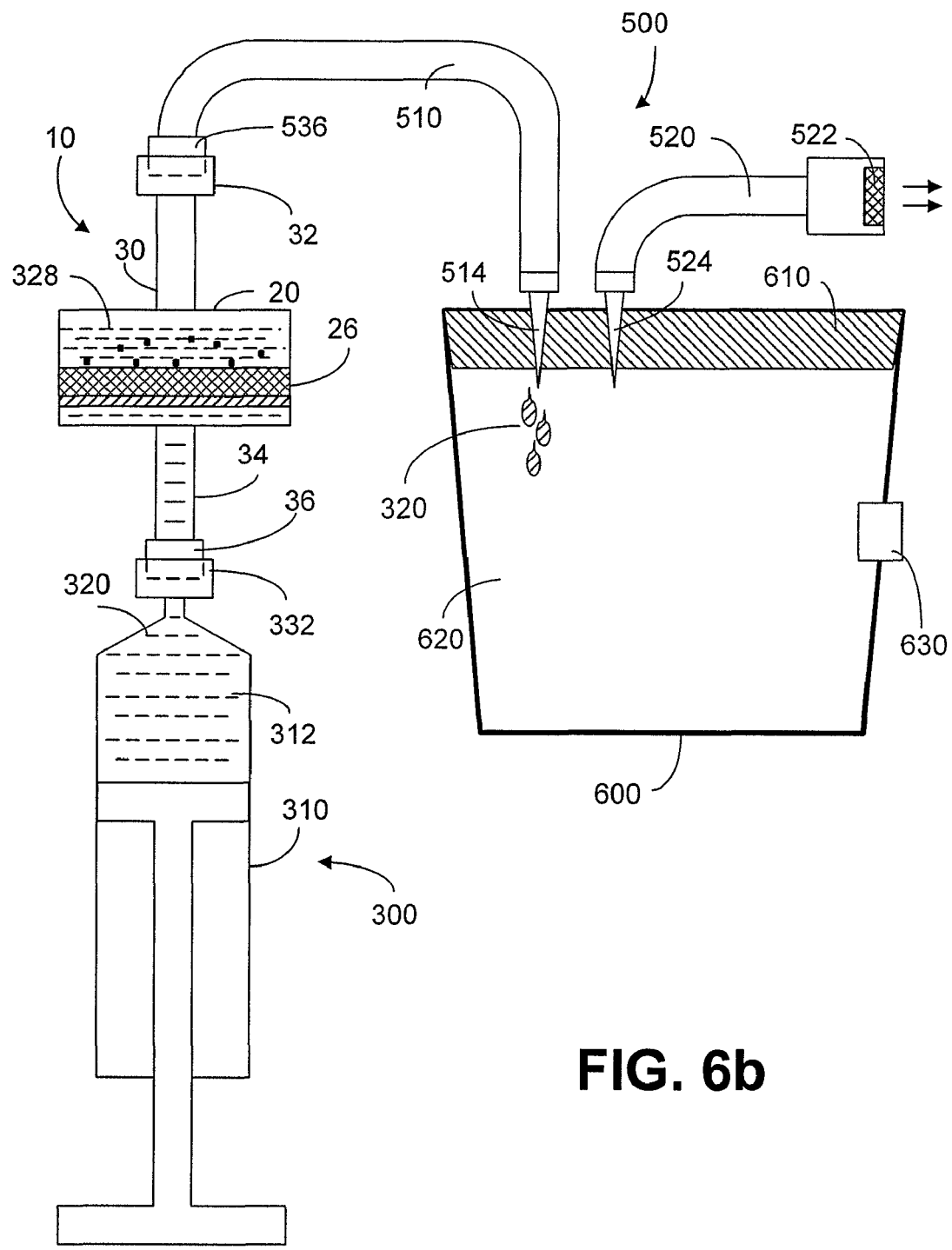
FIG. 6*b* is a schematic representation illustrating part of the hydration solution is injected into the filter collection assembly for hydrating the collected particles.

In a different embodiment, the transfer system 500 is securely attached to the test cartridge 600 as an integral part thereof. It is also possible that before the liquid injection system 300 is used to inject the hydration solution into the filter chamber 20, the first passageway 30 is directly connected to the transfer system 500 with the coupler 32 engaged with the coupler 536, as shown in FIG. 6a. The collection assembly 10 is then partially filled with the hydration solution 320, as shown in FIG. 6b. After the filter chamber 20 is agitated to further dislodge the collected particles from the filter 26, additional solution is injected into the collection assembly in order to push part of the hydration solution 320 inside the filter chamber 20 into the test cartridge 600, as shown in FIG. 4. The hydration solution can be distilled water or a buffer solution.

In another embodiment, the collection assembly 10 and the transfer system are integrated with the test cartridge 600 as a single functional unit, thereby eliminating the need for many of the self-sealing couplers. While the Cepheid GeneXpert System is designed for use with stand alone test cartridges, a low profile transfer device 500 could be attached on top of the test cartridge 600 and left in place as it is placed into the analysis device. Thin tubes and structural connections could be aligned to exit through the gaps around the GeneXpert door (or the door could be removed/modified) so that the collection, transfer, and test device could remain as a single sealed unit even during sample analysis.

Figure 7:
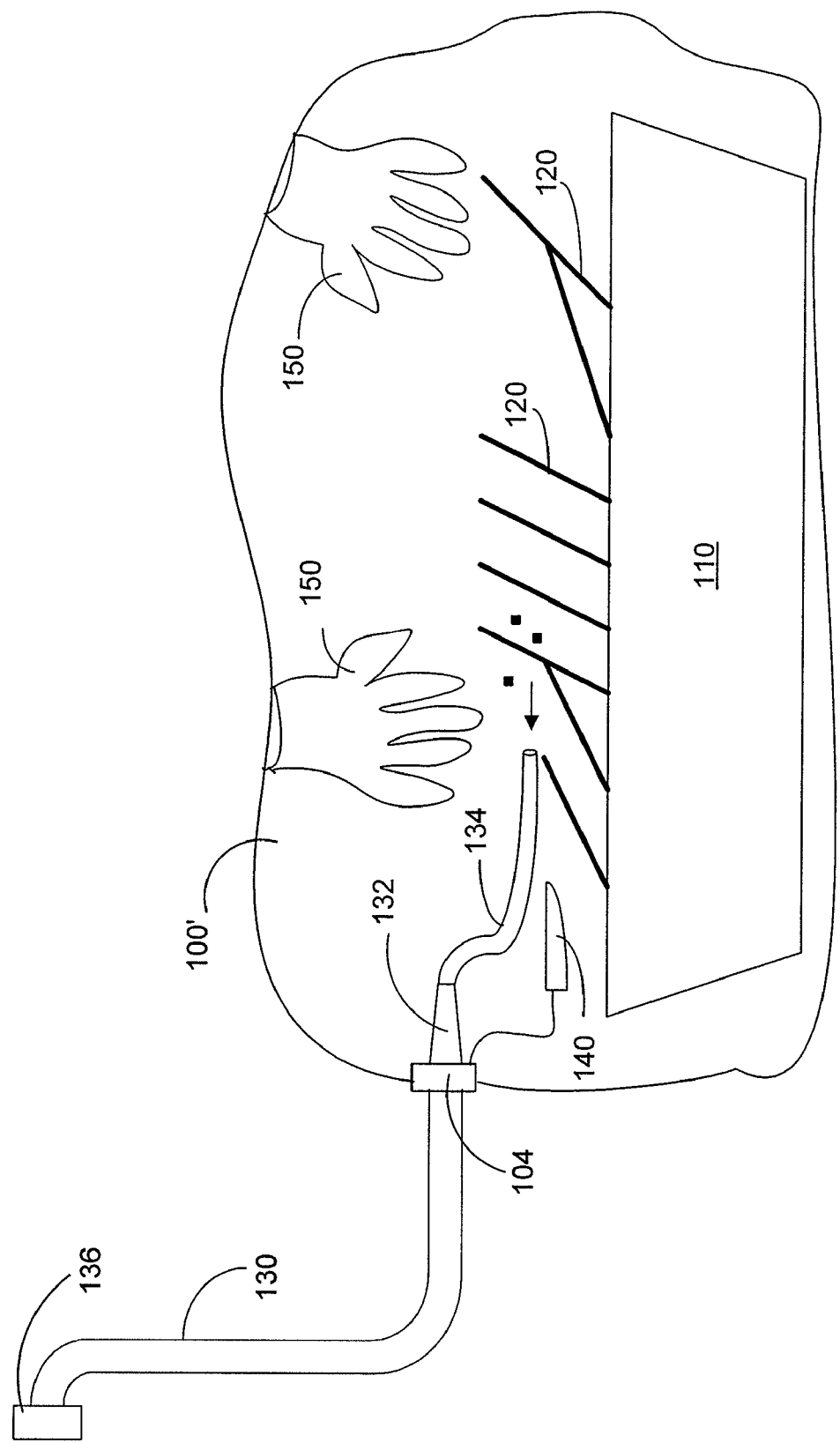
FIG. 7 is a schematic representation illustrating a glove bag used as a mailbag.

It is possible that the mailbag 100' is a glove bag having a pair of gloves 150 so as to allow a person to access the mailpieces 120 inside the bag 100' through the gloves, as shown in FIG. 7. A flexible tube 134 is extended from the inlet 132 so that it can be inserted into each of the mailpieces 120 for directly collecting particles in individual mailpieces. It is also possible to provide a cutter 140 inside the mailbag 100' to make a small slit cut on the mailpieces so as to allow the flexible tube 134 to be inserted into the slit cut.

Figure 8:
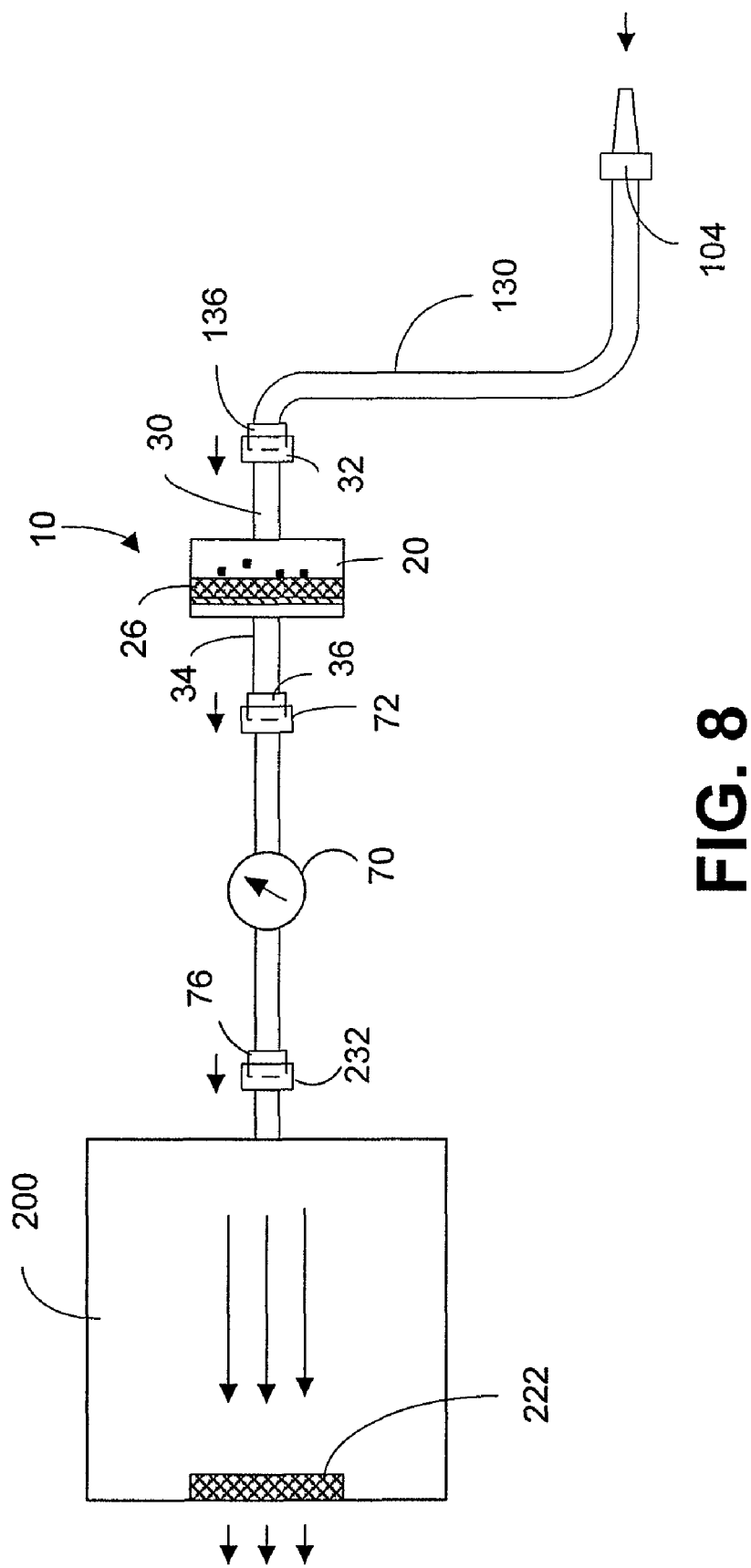
FIG. 8 is a schematic representation illustrating a airflow gauge being used in conjunction with an air pump system.

It is advantageous to install a flow gauge in the filter collection assembly to monitor the air flow. For example, an air flow gauge 70 having couplers 72 and 76 is installed between the air pump system 200 and the collection assembly 10, as shown in FIG. 8. The air flow gauge 70 could be a valuable element in that it provides a confirmation that air is being successfully sampled from the mailbag 100. The gauge 70 also provides objective demonstration of the air flow rate (6 liters per minute, for example). If the air flow is blocked, this may indicated that the tubing is kinked, the mailbag has been completely evacuated, or the self-sealing couplers are not properly engaged. For example, flow gauge 20 SCFH with tube fittings from King Instrument Company (Garden Grove, Calif.) can be used for such purposes. The air flow gauge may provide audio indication that the flow is not normal.

Figure 9:
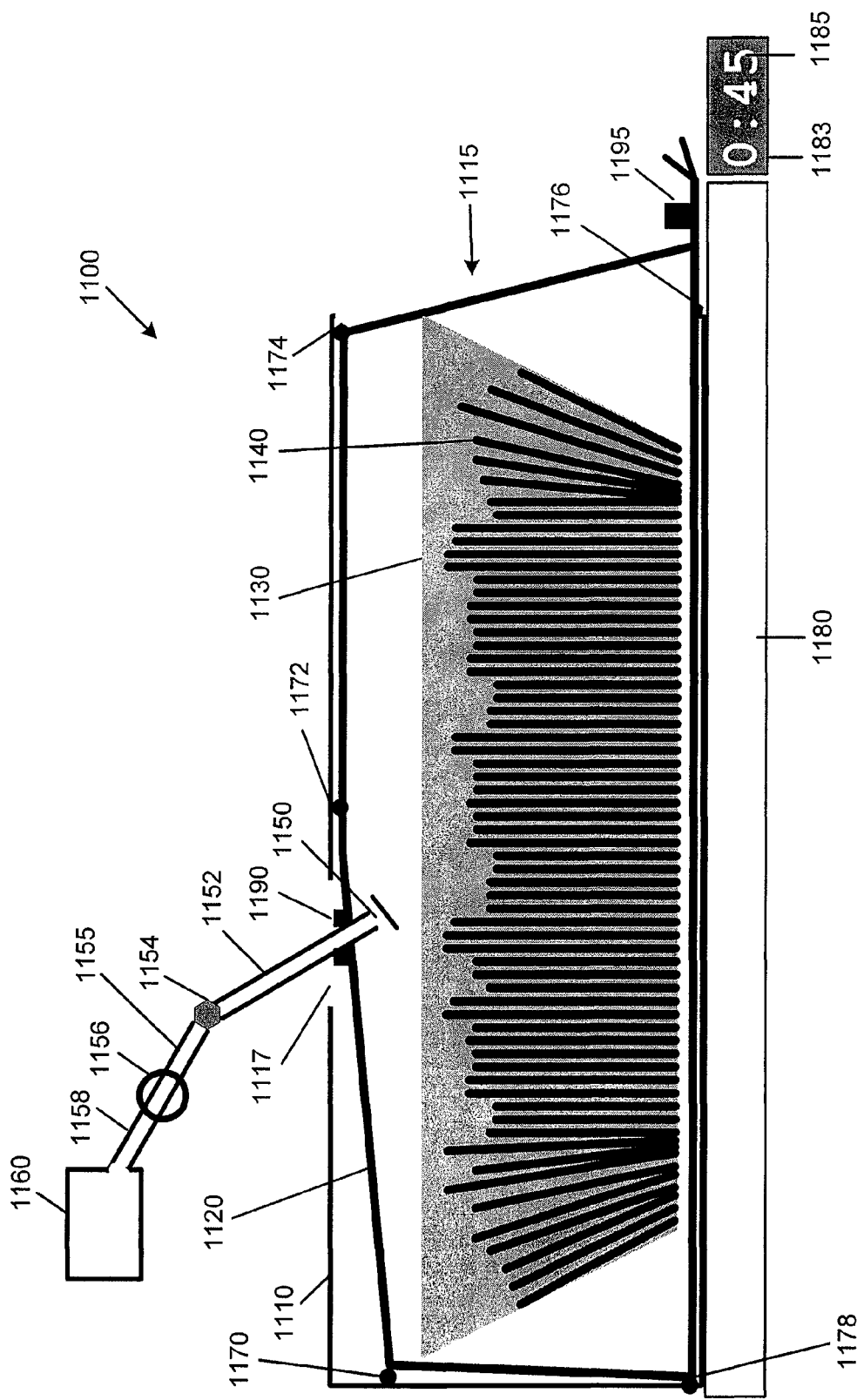
FIG. 9 is a schematic representation illustrating an alternative system for collecting and transferring biohazard samples according to another illustrative embodiment of the present application.

Referring to FIG. 9, a schematic representation illustrating an alternative system 1100 for collecting and transferring biohazard samples according to another illustrative embodiment of the present application is shown. The system 1100 is illustrated in a side view cross section. A rectangular box 1110 or other suitably shaped box to contain trays 1130 is constructed of a suitable material such as a clear Plexiglas closed on 5 sides and open on one side, e.g. the right side 1115 (or with a door that may open). The opening 1115 (or door) provides the opening to the so called garage (the box 1110) in which the trays of mail 1130 will be parked for sampling in an anti-static container 1120 such as an anti-static bag. Here, the garage is lined with a replaceable plastic anti-static bag 1120. The inside of the plastic bag should contain no new materials beyond those included in any initial spore test. Accordingly, it may be advantageous to have the bag inside the rigid structure, rather than having the rigid structure inside the bag. It is preferable that aerosolized spores not be attracted to or stick to the garage material. Therefore, the bag 1120 is attached to the inside of the box by fasteners such as glue, or removable fasteners such as clamps or VELCRO hook and eye fasteners 1170, 1172, 1174, 1176, 1178 to keep the bag expanded to the rough dimensions of the rigid garage 1110. Such bags have been tested as part of a Biohazard Isolation and Screening system (BISS) and are now known to be capable of use for the containment and collection of biohazard spores. A sample collection tube 1152 with a "T" shaped end 1150 is inserted into the top of the bag and sealed with a tie wrap or clamp 1190. The branched air inlet 1150 helps ensure that it cannot be blocked if the end makes contact with the plastic bag material. The sample collection tube 1152 passes out of the garage 1110 through a hole 1117, to the pharmaceutical self sealing connector 1154. It continues through tube 1155 to the sample collection filter 1156 and then though an additional tube 1158 to the BISS handheld vacuum unit 1160. The antistatic bag 1120 and the sample collection components 1150, 1152, 1154, 1155, 1156, 1158, and 1160 are described more fully above and in the related incorporated applications. The present illustrative embodiment uses many of the features and materials described as effective in the related applications even though the external appearance and operational processes have been modified to reflect the different operating environment for this configuration.

In operation, a mail tray 1130 containing a plurality of mail pieces 1140 is placed inside the anti-static plastic bag 1120. The plastic bag 1120 is then sealed shut with a tie wrap, Velcro strap, or preferably a hinging bar 1195 which folds down to seal the bag shut across the entire length of the opening. Such a closure device 1195 can be operated quickly with one hand. Alternatively, a rubber lining on the edge against the plastic bag would ensure that a tight form fit could be maintained to make a good seal. The entire garage 1110 is rigidly attached to a jogger platform 1180 which allows the garage, bag, mail tray, and mail pieces to be agitated and thereby aerosolize spores within the mail for collection on the BISS filter 1154 when air is drawn by the handheld vacuum 1160. One useful protocol provides for the mail to be agitated for 45 seconds after which the clamp 1195 may be released. The mail tray 1130 containing mail 1140 may then be removed through the opening 1115 and another tray inserted into the station to repeat the process. Use of two such jogger/collection stations would allow the pharmaceutical connector 1154 to be disconnected from the first station and connected to a tray loaded into the second station for collection while the first station was being reloaded. In this manner, system throughput can be maintained with a tray being processed every 45 seconds (the sample collection time). As soon as one tray collection is complete, the tube is switched to the other work station and collection commences there with barely a second of delay. The operator then has nearly 45 seconds to exchange mail trays in the first station. This task would be expected to require only 5 or 10 seconds, thereby allowing an operator sufficient time for staging trays, delivering them to the adjacent work flow processes, or data recording while the pump runs continuously.

A smooth work surface 1183—possibly with rollers—at the same elevation as the "garage" floor would allow the trays to be slid into the ergonomic biohazard sampling station without the need for any additional lifting. A resetable digital timer 1185 allows the operator to time the samples and observe how much time remains on the current sampling cycle. The biohazard work station 1100 could be easily operated by a single employee. At 45 seconds per tray, the employee would be able to process approximately 80 trays per hour. Such efficiency compares very favorably with prior testing processes that often require considerably more hardware and an additional operator. This embodiment and alternatives described and referred to may be utilized with any of the embodiments described and referred to in the incorporated related applications as practical.

It should be also noted that the filter collection system, according to the present invention, allows for the creation of a sample volume greater than that required for a single test run so that the same sample can be used for re-testing if needed.

Thus, although the invention has been described with respect to a preferred embodiment thereof, it will be understood by those skilled in the art that the foregoing and various other changes, omissions and deviations in the form and detail thereof may be made without departing from the scope of this invention.

What is claimed is:

1. A method for collecting particles that may be contaminants from the air in a container, comprising:
    providing a collection assembly having a filter chamber;
    operatively connecting the collection assembly to the container;
    agitating the container;
    while agitating the container, drawing at least part of the air from the container through the filter chamber of the collection assembly so as to collect in the filter chamber the particles in the air drawn from the container; and
    mixing in the filter chamber at least part of the collected particles with a liquid.

2. The method of claim 1, wherein the collected particles are transferred to a test cartridge for testing, said method further comprising:
    operatively connecting the collection assembly to the test cartridge; and
    moving at least part of the liquid in the filter chamber to the test cartridge.

3. The method of claim 2, further comprising
    agitating the liquid in the filter chamber prior to said moving so as to increase the part of the collected particles mixed with the liquid.

4. The method of claim 1, further comprising
    injecting the liquid into the filter chamber after said drawing and prior to said mixing.

5. The method of claim 4, wherein the liquid injected into the filter chamber is substantially retained in the filter chamber in said mixing.

6. The method of claim 2, wherein
    the collection assembly has a first passageway and a second passageway separately extended from the filter chamber, and wherein
    the first passageway is operatively connected to the container for operatively connecting the collection assembly to the container, said method further comprising
    operatively connecting the second passageway to an air drawing system for drawing said part of the air from the container through the first passageway, the filter chamber and then the second passageway.

7. The method of claim 6, further comprising
    disconnecting the second passageway from the air drawing system after said drawing, and
    operatively connecting the second passageway to a liquid providing device so as to allow the liquid providing device to provide the liquid in the filter chamber through the second passageway prior to said mixing.

8. The method of claim 7, further comprising
disconnecting the first passageway from the container after said drawing; and
operatively connecting the first passageway to the test cartridge for operatively connecting the collection assembly to the test cartridge.

9. The method of claim 8, further comprising
further providing a further amount of liquid to the second passageway after said mixing and operatively connecting the first passageway to the test cartridge so as to move said at least part of the liquid in the filter chamber to the test cartridge.

10. The method of claim 7, wherein the amount of the liquid provided to the filter chamber by the liquid providing device is predetermined to suit the size of the filter chamber and the second passageway.

11. The method of claim 1, further comprising
disturbing the container so as to stir up the particles in the container into the air in the container.

12. The method of claim 1, wherein
the container containing one or more mailpieces, said method further comprising
disturbing said one or more mailpieces so as to stir up the particles associated with said one or more mailpieces.

13. A method for collecting particles that may be contaminants from the air in an antistatic lined resealable container, comprising:
providing a collection assembly having a filter chamber;
operatively connecting the collection assembly to the container;
agitating the container;
while agitating the container, drawing at least part of the air from the container through the filter chamber of the collection assembly so as to collect in the filter chamber the particles in the air drawn from the container as a sample; and
subsequently transferring the sample to an analysis device.

14. The method of claim 13, wherein,
the container is resealed with a door.

15. The method of claim 13, wherein,
the container is resealed with a clamping device around the antistatic lining.

16. The method of claim 13, wherein,
the container is resealed with a reusable fastener.

17. The method of claim 13, wherein,
the container is resealed with a tie wrap.

18. A method for collecting particles that may be contaminants from the air in a container, comprising:
providing a collection assembly having a filter chamber;
operatively connecting the collection assembly to the container;
drawing at least part of the air from the container through the filter chamber of the collection assembly so as to collect in the filter chamber the particles in the air drawn from the container; and
mixing in the filter chamber at least part of the collected particles with a liquid, wherein,
the collected particles are transferred to a test cartridge for testing, said method further comprising:
operatively connecting the collection assembly to the test cartridge;
moving at least part of the liquid in the filter chamber to the test cartridge;
agitating the liquid in the filter chamber prior to said moving so as to increase the part of the collected particles mixed with the liquid; and
providing beads in the filter chambers for agitating the liquid in the filter chamber.

19. The method of claim 1, further comprising:
before mixing in the filter chamber at least part of the collected particles with a liquid,
operatively connecting the collection assembly to a second container; and
drawing at least part of the air from the second container through the filter chamber of the collection assembly so as to collect in the filter chamber the particles in the air drawn from the second container.

20. The method of claim 19, further comprising:
while drawing at least part of the air from the second container, agitating the second container.

* * * * *